United States Patent [19]

Parsons et al.

[11] Patent Number: 4,731,444

[45] Date of Patent: Mar. 15, 1988

[54] BICYCLIC LACTAMS AS ANTIHYPERTENSIVES

[75] Inventors: William H. Parsons, Rahway; Matthew J. Wyvratt, Jr., Mountainside, both of N.J.

[73] Assignee: Merck & Co., Inc., Rahway, N.J.

[21] Appl. No.: 637,622

[22] Filed: Aug. 3, 1984

[51] Int. Cl.⁴ .................... C07D 513/04; A61K 31/35
[52] U.S. Cl. .................................................... 540/521
[58] Field of Search .................. 260/239.3 B; 540/521

[56] References Cited

U.S. PATENT DOCUMENTS 4,415,496 11/1983 Harris et al. ................. 260/239.3 B Primary Examiner—Robert T. Bond
Attorney, Agent, or Firm—Salvatore C. Mitri; Michael C. Sudol; Mario A. Monaco

[57] ABSTRACT

There are disclosed bicyclic lactams and derivatives thereof which are useful as converting enzyme inhibitors and as antihypertensives.

1 Claim, No Drawings

BICYCLIC LACTAMS AS ANTIHYPERTENSIVES

BACKGROUND OF INVENTION

This invention is directed to bicyclic lactams and derivatives thereof which are useful as converting enzyme inhibitors and as antihypertensives. The compounds of this invention are represented by the following formula:

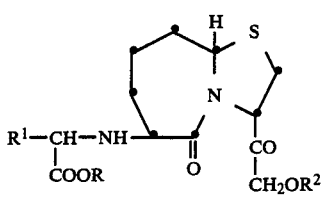

wherein:
R is hydrogen, loweralkyl, aryl, and aralkyl;
$R^1$ is hydrogen; hydrocarbon of from 1 to 12 carbon atoms which include branched and unsaturated alkyl groups (such as 3-methyl-1-butyl, 3,3-dimethylallyl, and the like); cycloalkyl of $C_3$-$C_{10}$ (such as cyclohexylethyl); substituted lower alkyl wherein the substituent can be halo, hydroxy, carboxy, lower alkylthio, lower alkoxy, lower alkoxy carbonyl, lower aralkoxy carbonyl, amino, lower alkylamino, lower dialkylamino, or acylamino; substituted lower alkyl having the formula $R_A(CH_2)_n$—Q—$(CH_2)_m$ wherein n is 0-2, m is 1-3, $R_A$ is aryl or heteroaryl optionally substituted by amino, lower dialkylamino, lower alkylamino, hydroxy, hydroxy loweralkyl, aminoloweralkyl, trihaloloweralkyl, cyano, nitro, sulfonamido, aroyl, lower alkyl, halo, dihalo, and lower alkoxy, and Q is O, S, N—$R_B$, $CONR_C$, $NR_CCO$, CH=CH wherein $R_B$ is hydrogen, loweralkyl, aryl, aralkyl, lower alkanoyl, or aroyl, and $R_C$ is hydrogen or lower alkyl; aryl (such as phenyl, naphthyl or biphenyl); substituted aryl wherein the substituent is lower alkyl, amino loweralkyl, loweralkoxy, aryloxy, aroyl, hydroxy, halo, or dihalo; aralkyl or heteroaralkyl which include branched lower alkyl groups (such as 2,2-dibenzylethyl); substituted aralkyl or substituted heteroaralkyl which include branched lower alkyl groups wherein the lower alkyl groups can be substituted by amino, acylamino, or hydroxyl and the aryl and heteroaryl groups can be substituted by halo, dihalo, loweralkyl, hydroxy, loweralkoxy, aryloxy, aroyl, arylthio, amino, amino lower alkyl, lower alkanoylamino, aroylamino, lower dialkylamino, lower alkylamino, hydroxy, hydroxy loweralkyl, trihalo loweralkyl, nitro, cyano, or sulfonamido;
$R^2$ is hydrogen, loweralkanoyl or arloweralkanoyl; and,
the pharmaceutically acceptable salts thereof.

The lower alkyl groups, except where noted otherwise, represented by any of the variables include straight, branched and unsaturated chain hydrocarbon radicals from one to six carbon atoms, for example, methyl, ethyl, propyl, isopropyl, butyl, isobutyl, t-butyl, pentyl, isopentyl, hexyl or vinyl, allyl, butenyl and the like. The aralkyl and heteroaralkyl groups represented by any of the above variables have from one to six carbon atoms in the alkyl portion thereof and include for example, benzyl, phenethyl, 3,3-diphenylpropyl, 3-indolylmethyl, and the like. Halo means chloro, bromo, iodo or fluoro. Aryl where it appears in any of the radicals, except where noted, represents phenyl, naphthyl, or biphenyl. Aroyl includes benzoyl, 1-naphthoyl, and the like. Heteroaryl includes, for example, indolyl, thienyl, imidazolyl, furyl, benzimidazolyl, pyridyl, quinolinyl, isoquinolinyl, and benzothienyl. Acylamino refers to lower alkanoylamino and aroylamino groups such as, for example, acetylamino, benzoylamino, and the like. Hetero denotes a single O, N or S atom and halo denotes chlorine, bromine or iodine.

The products of Formula 1 can be produced as shown in the following Reaction Scheme wherein R, $R^1$, and $R^2$ are as defined above.

REACTION SCHEME

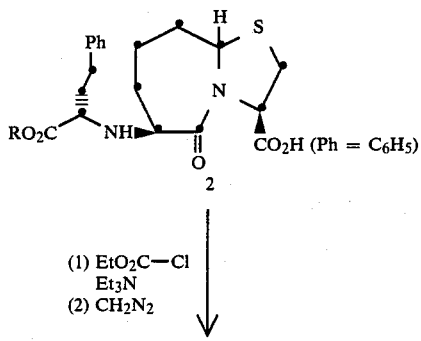

REACTION SCHEME
-continued

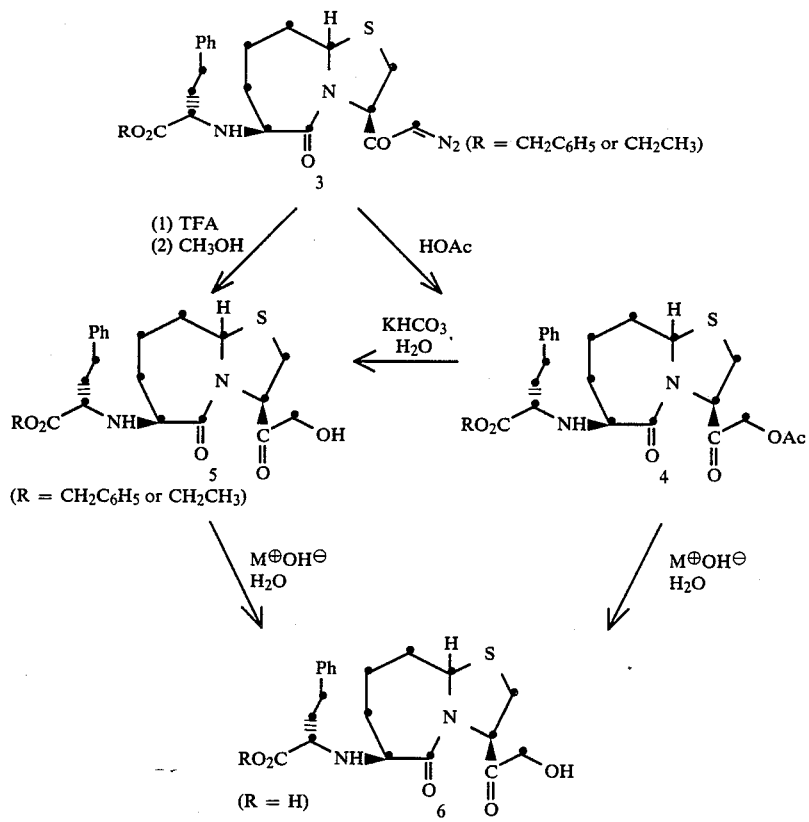

As shown in the foregoing Reaction Scheme, thiabicyclic lactam 2, prepared according to the methods disclosed in U.S. Pat. No. 4,415,496 can be reacted with an alkoxy chloroformate such as ethyl chloroformate (EtO$_2$C—Cl) or isobutyl chloroformate and a tertiary amine such as triethylamine (Et$_3$N) or N-methylmorpholine in a suitable organic solvent such as tetrahydrofuran (THF), dimethoxyethane (DME) or ether to provide, upon removal of the trialkylamine hydrochloride, a mixed anhydride which, upon reaction with diazomethane in ether, gives the diazoketone compound 3. Refluxing diazoketone 3 in acetic acid (HOAc) affords acetate 4. Subsequent treatment of acetate 4 with a metal hydroxide such as potassium hydroxide in water gives hydroxyketone acid 6.

Alternatively, diazoketone 3 can be reacted in trifluoroacetic acid (TFA) followed by hydrolysis with methanol to afford hydroxymethyl ketone ester 5. Hydrolysis of 5 with sodium hydroxide or potassium hydroxide in water affords hydroxyketone acid 6.

If the ester in 5 is a benzyl group, Compound 5 can be hydrogenated in a protic solvent such as ethanol in the presence of a catalyst such as palladium on cardon to obtain hydroxy ketone acid 6.

Also, acetate 4 can be converted to ester 5 by hydrolysis of acetate 4 with sodium bicarbonate or potassium bicarbonate in water.

Preferred diastereomers are isolated by chromatography or crystallization of intermediates or the end products or their salts. If desired, compounds of this invention can also be employed as a mixture of diastereomers.

The α-keto acids and α-keto esters utilized in the process of the invention are known in the art or can be made by numerous, known methods. For example, synthons such as can be converted to α-keto acids or esters using methods involving alkylation followed by hydrolysis as described in the literature. An excellent method involves the reaction of Grignard reagents R$^1$MgX with ClCO-CO$_2$Y or YO$_2$CCO$_2$Y. Another method involves condensing substituted acetic acid esters with diethyl oxalate followed by hydrolytic decarboxylation under acidic conditions to obtain α-keto acids. Carefully controlled acid hydrolysis in alcohol of acyl cyanides, which are prepared from acid chlorides and cuprous cyanide, also proves to be a viable synthetic route to α-keto esters. Nucleophilic displacement reactions on chloro or bromo pyvuric acid (ester) can also be used to produce a variety of interesting α-keto acids (esters). In these formulae, Y is a group such as loweralkyl or benzyl and protecting groups are employed as necessary in the R$^1$ group if interfering functionality is present.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases e.g., dicyclohexylamine salts, N-methyl-D-glucamine, salts with amino acids like arginine, lysine and the like. Also salts with organic and inorganic acids may be prepared, e.g., HCl, HBr, $H_2SO_4$, $H_3PO_4$, methanesulfonic, toluenesulfonic, maleic, fumaric, camphorsulfonic. The non-toxic physiologically acceptable salts are preferred, although other salts are also useful, e.g., in isolating or purifying the product.

The salts may be formed by conventional means as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

The compounds of this invention inhibit angiotensin converting enzyme and thus block conversion of the decapeptide angiotensin I to angiotensin II. Angiotensin II is a potent pressor substance. Thus, blood-pressure lowering can result from inhibition of its biosynthesis especially in animals and humans whose hypertension is angiotensin II related. Furthermore, converting enzyme degrades the vasodepressor substance, bradykinin. Therefore, inhibitors of angiotensin converting enzyme may lower blood-pressure also by potentiation of bradykinin. Although the relative importance of these and other possible mechanisms remains to be established, inhibitors of angiotensin converting enzyme are effective antihypertensive agents in a variety of animal models and are useful clinically, for example, in many human patients with renovascular, malignant and essential hypertension. See, for example, D. W. Cushman et al., *Biochemistry* 16, 5484 (1977).

The evaluation of converting enzyme inhibitors is guided by in vitro enzyme inhibition assays. For example, a useful method is that of Y. Piquilloud, A. Reinharz and M. Roth, *Biochem. Biophys. Acta,* 206, 136 ( 1970) in which the hydrolysis of carbobenzyloxyphenylalanylhistidinylleucine is measured. In vivo evaluations may be made, for example, in normotensive rats challenged with angiotensin I by the technique of J. R. Weeks and J. A. Jones, *Proc. Soc. Exp. Biol. Med.,* 104, 646 (1960) or in a high renin rat model such as that of S. Koletsky et al., *Proc. Soc. Exp. Biol. Med.* 125, 96 (1967).

Thus, the compounds of this invention are useful as antihypertensives in treating hypertensive mammals, including humans, and they can be utilized to achieve the reduction of blood pressure by formulating in compositions such as tablets, capsules or elixirs for oral administration or in sterile solutions or suspensions for parenteral administration. The compounds of this invention can be administered to patients in need of such treatment in a dosage range of 0.5 to 100 mg per patient generally given several times, thus giving a total daily dose of from 0.5 to 400 mg per day. The dose will vary depending on severity of disease, weight of patient and other factors which a person skilled in the art will recognize.

It is often advantageous to administer compounds of this invention in combination with other antihypertensives and/or diuretics and/or calcium entry blockers. For example, the compounds of this invention can be given in combination with such compounds as amiloride, atenolol, bendroflumethiazide, chlorothalidone, chlorothiazide, clonidine, cryptenamine acetate and cryptenamine tannates, deserpidine, diazoxide, ethacrynic acid, furosemide, guanethidene sulfate, hydralazine hydrochloride, hydrochlorothiazide, hydroflumethiazide, metolazone, metoprolol tartate, methylclothiazide, methyldopa, methyldopate hydrochloride, minoxidil, (S)-1-{[2-(3,4-dimethoxyphenyl)ethyl]amino}-3-{[4-(2-thienyl)-1H-imidazol-2-yl]phenoxy}-2-propanol, polythiazide, the pivaloyloxyethyl ester of methyldopa, indacrinone and variable ratios of its enantiomers, nifedipine, verapamil, diltiazam, flumethiazide, bendroflumethiazide, atenolol, (+)-4-{3-{-[2-(1-hydroxycyclohexyl)ethyl]-4-oxo-2-thiazolidinyl}propyl}benzoic acid, bumetanide, prazosin, propranolol, *rauwolfia serpentina,* rescinnamine, reserpine, spironolactone, timolol, trichlormethiazide, benzthiazide, quinethazone, tricrynafan, triamterene, acetazolamide, aminophylline, cyclothiazide, merethoxylline procaine, bepridil, diltiazim, etafenone, falipamiL, felodipine, flunarizine, gallopamiL, inadapamide, lidoflazine, nicardipine, nifedipine, nimodipine, nitrendipine, perhexaline, prenylamine, tiapamil, verapamil, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the antihypertensives of this invention effective clinically in the 0.5-100 milligrams per day range can be effectively combined at levels at the 0.1-100 milligrams per day range with the following compounds at the indicated per day dose range: hydrochlorothiazide (10-100 mg), timolol (5-60 mg), methyldopa (65-2000 mg), the pivaloyloxyethyl ester of methyldopa (30-1000 mg), indacrinone and variable ratios of its enantiomers (25-150 mg) and (+)-4-{3-{[2-(1-hydroxycyclohexyl)ethyl]-4-oxo-2-thiazolidinyl}propyl}-benzoic acid (10-100 mg).

In addition, the triple drug combinations of hydrochlorothiazide (10-100 mg) plus timolol (5-60 mg) plus converting enzyme inhibitor of this invention (0.5-100 mg) or hydrochlorothiazide (10-100 mg) plus amiloride (5-20 mg) plus converting enzyme inhibitor of this invention (0.5-100 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, the combinations shown above are formulated into pharmaceutical compositions as discussed below.

About 0.1 to 50 mg of a compound or mixture of compounds of Formula 1 or a physiologically acceptable salt can be compounded with other conventional pharmaceutically acceptable compounding ingredients, as necessary or desired. Such ingredients are generally referred to as carriers or diluents. Conventional procedures for preparing such compositions in appropriate dosage forms can be utilized. Whatever the dosage form, it will contain a pharmaceutically effective amount of the present composition.

The present compositions can be administered orally or other than orally; e.g., parenterally, by insufflation, topically, rectally, etc.; using appropriate dosage forms; e.g., tablets, capsules, suspensions, solutions, and the like, for oral administration; suspension emulsions, and the like, for parenteral administration; solutions for intravenous administration; and ointments, transdermal patches, and the like, for topical administration.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be for example, (1) inert diluents such as calcium carbonate, sodium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions.

Such excipients may be
  (1) suspending agents such as sodium carboxymethylcellulose, methylcellulose, hydroxypropylmethylcellulose, sodium alginate, polyvinylpyrrolidone, gum tragacanth and gum acacia;
  (2) dispersing or wetting agents which may be
    (a) a naturally-occurring phosphatide such as lecithin,
    (b) a condensation product of an alkylene oxide with a fatty acid, for example, polyoxyethylene stearate,
    (c) a condensation product of ethylene oxide with a long chain aliphatic alcohol, for example, heptadecaethyleneoxycetanol,
    (d) a condensation product of ethylene oxide with a partial ester derived from a fatty acid and a hexitol such as polyoxyethylene sorbitol monooleate, or
    (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

A composition of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compositions of the invention are employed.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following examples are illustrative of the best mode presently known for practicing the invention and constitute especially preferred embodiments and should, therefore, not be construed as being limitative of the invention. The preferred diastereomers of these examples are isolated by conventional column chromatography or fractional crystallization. Unless otherwise indicated, all temperatures are in degrees Celsius.

EXAMPLE 1

6(S)-[1(S)-(Benzyloxycarbonyl-3-phenylpropyl-)amino]octahydro-5-oxo-9a(R)-thiazolo[3,2-a]azepine-3-(R)[2-diazo-1-oxoethane]

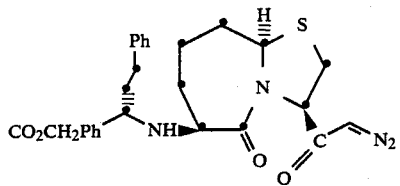

To a solution of 6(S)-[1(S)benzyloxycarbonyl-3-phenylpropyl)amino]octahydro-5-oxo-9a(R)-thiazolo[3,2-a]azepine-3-(R)-carboxylic acid (0.315 g) in 7.5 ml of THF at −10° C. was added 0.085 ml of isobutyl chloroformate, followed by 0.072 ml of N-methyl morpholine. After stirring at −10° C. for 15 minutes, the reaction mixture was filtered in a nitrogen atmosphere. To the THF solution at −10° C. was added a solution of diazomethane in ether [prepared from 1 gm of N-nitrosomethylurea was reported in *Organic Synthesis*, Coll. Vol. II pg 165] and the solution was stirred 12 hours at 0° C. The crude reaction mixture was evaporated at reduced pressure and chromatographed (silica, 2:1 ethyl acetate:hexanes) to afford 0.312 gm of product.

TLC (silica, 2:1 ethyl acetate:hexanes) $R_f=0.37$.

NMR(CDCl$_3$, TMS, 200 MHz) δ1.5–2.2 (m, 8H); 2.65 (t, 2H); 2.9–3.1 (m, 1H); 3.2–3.4 (m, 3H); 3.69 (m, 1H); 4.8 (m, 1H), 5.1 (m, 1H); 5.2 (s, 2H); 5.5 (s, 1H); 7.22 (m, 5H); 7.45 (m, 5H).

EXAMPLE 2

6(S)-[1(S)-(Ethoxycarbonyl-3-phenylpropyl)amino]octahydro-5-oxo-9a(R)-thiazolo[3,2-a]azepine-3-(R)[2-diazo-1-oxoethane]

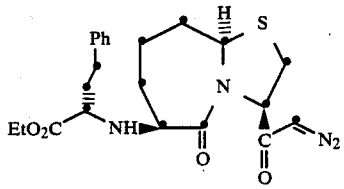

To a solution of 6(S)-[1(S)ethoxycarbonyl-3-phenylpropyl)amino]octahydro-5-oxo-9a(R)-thiazolo[3,2-a]azepine-3(R)carboxylic acid (0.110 g) in 3 ml of THF at −10° C. was added dropwise 0.026 ml of ethylchloroformate followed by 0.036 ml of triethylamine. After stirring at −10° C. for 15 minutes, the reaction mixture was filtered in a nitrogen atmosphere. To the THF solution at −10° C. was added a solution of diazomethane in ether [prepared from 0.5 gm of N-nitrosomethylurea as reported in *Organic Synthesis*, Coll. Vol. II. pg 165] and the solution was stirred for 12 hours at 0° C. The crude reaction mixture was evaporated at reduced pressure and chromatographed (silica, 2:1, ethyl acetate:hexanes) to give 121 mg of product. TLC (silica, 2:1, ethyl acetate:hexane) $R_f=0.43$ NMR (CDCl$_3$, TMS) δ1.3 (t, 3H); 1.6–2.3 (m, 8H); 2.6–2.9 (m, 2H); 3.1–3.6 (m, 4H); 4.2 (q, 2H); 4.9–5.2 (m, 3H); 5.5 (s, 1H); 7.2 (s, 5H).

EXAMPLE 3

6(S)-[1(S)-(Benzyloxycarbonyl-3-phenylpropyl-)amino]octahydro-5-oxo-9a(R)-thiazolo[3,2-a]azepine-3-(R)-[2-hydroxy-1oxoethane]

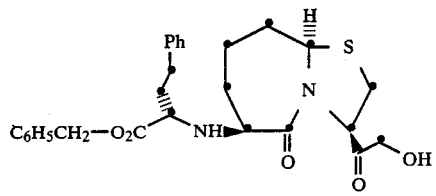

To a solution of the diazoketone benzyl ester (0.312 g) of Example 1 in 10 ml of methylene chloride at room temperature was added 5 ml of trifluoroacetic acid. After 1 hour at room temperature during which gas evolution (N$_2$) was observed, the solvents were removed at reduced pressure. The crude reaction mixture was dissolved in 5 ml of methanol and the solution was stirred 12 hours at room temperature. After removal of methanol in vacuo, the crude product was chromatographed (silica, ethyl acetate) to give 0.202 gm of product.

TLC (silica, ethyl acetate) $R_f=0.38$.

NMR (CDCl$_3$, TMS) δ1.4–2.2 (m, 8H); 2.7 (t, 2H); 3.1 (m, 1H); 3.2–3.5 (m, 3H); 4.4 (s, 2H); 4.65 (m, 1H); 5.15–5.35 (m, 3H); 7.2–7.5 (m, 10H).

EXAMPLE 4

6(S)-[1(S)-(Ethoxycarbonyl-3-phenylpropyl)amino]octahydro-5-oxo-9a(R)-thiazolo[3,2-a]azepine-3-(R)-[2-hydroxy-1-oxoethane].

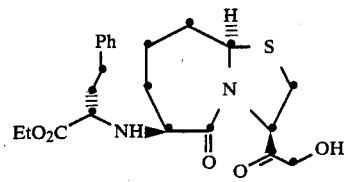

A solution of 0.117 gm of the diazoketone ethylester of Example 2 in 5 ml of trifluoroacetic acid was stirred at room temperature for 2 hours during which gas(N$_2$) evolved. Upon concentration at reduced pressure, the crude reaction mixture was redissolved in 5 ml of ethanol and stirred for 12 hours at room temperature. After concentration in vacuo, the crude product was chromatographed (silica, ethyl acetate) yielding 18.6 mg of product.

TLC (silica 1.5:1 ethyl acetate:hexanes) $R_f=0.23$.

NMR (CDCl₃, TMS) δ1.35 (t, 3H); 1.5–2.2 (m, 8H); 2.73 (t, 2H); 3.1 (m, 1H); 3.3–3.6 (m, 3H); 4.2 (q, 2H); 4.4 (ABq, 2H); 5.0 (m, 1H); 5.2 (m, 1H); 7.2–7.35 (m, 5H). Mass spectrum M+435.

EXAMPLE 5

6(S)-[1(S)-(Carboxy-3-phenylpropyl)amino]octahydro-5-oxo-9a(R)-thiazolo[3,2-a]azepine-3-(R)[2-hydroxy-1-oxo ethane]

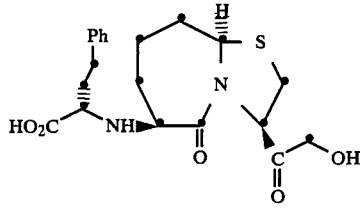

A solution of 0.027 gm of the hydroxy methylketone benzyl ester of Example 3 in 5 ml of 95% ethanol and 0.0066 ml of acetic acid with 28 mg of 10% Pd/C as catalyst was hydrogenated under 40 Psi of hydrogen for 12 hours. The reaction mixture was subsequently filtered and the filtrate concentrated in vacuo. The crude product was chromatographed. (silica, 1:1:1:1, ethyl acetate:acetic acid:n-butanol:H₂O] to give 5.2 mg of product.

TLC (silica, 1:1:1:1, ethyl acetate:acetic acid:n-butanol:H₂O) R_f=0.63.

NMR (DMSO, TMS) δ1.5–2.3 (m, 8H); 2.8 (m, 2H); 3.1–3.5 (m, 4H); 4.25 (s, 2H); 5.0–5.25 (m, 2H); 7.2–7.4 (m, 5H).

EXAMPLE 6

Additional Products of Formula I

Additional keto acids and keto esters listed in Table I below as well as those employed in the foregoing examples can be employed to yield, after removal of protecting groups, if any, products of Formula I listed below in Table II. In Table II, the stereochemistry at 9a refers to the hydrogen configuration being R or S at the ring structure in the bicyclic lactam part-structure of Formula I compounds.

TABLE I

KETO ACIDS AND KETO ESTERS OF THE FORMULA:
R¹COCO₂R
IX (a) 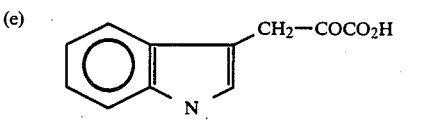

(b) 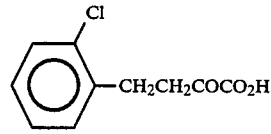

(c) 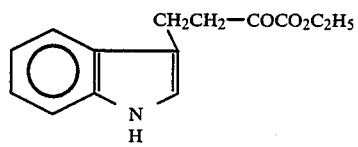

(d) 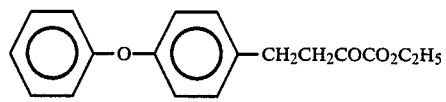

TABLE I-continued

KETO ACIDS AND KETO ESTERS OF THE FORMULA:
R¹COCO₂R
IX (e) 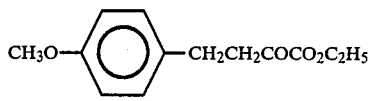

(f) 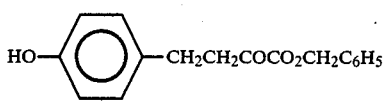

(g) 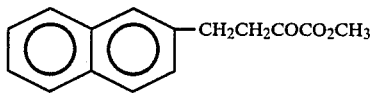

(h) 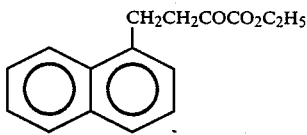

(i) 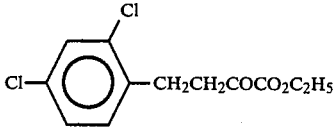

(j) 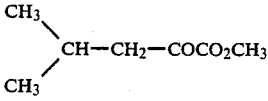

(k) 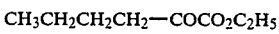

(l) 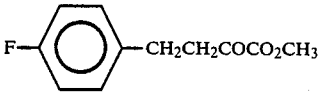

(m) 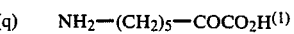

(n) CH₃
　　　＼
　　　　CH—CH₂—COCO₂CH₃
　　　／
　　CH₃

(o) CH₃CH₂CH₂CH₂—COCO₂C₂H₅

(p) F—⟨phenyl⟩—CH₂CH₂COCO₂CH₃

(q) NH₂—(CH₂)₅—COCO₂H⁽¹⁾

TABLE I-continued
KETO ACIDS AND KETO ESTERS OF THE FORMULA: $R^1COCO_2R$ IX (r) 2-(aminomethyl)phenyl-CH₂CH₂COCO₂H [structure with CH₂NH₂ on benzene ring, —CH₂CH₂COCO₂H](1)

(s) imidazolyl-CH₂CH₂COCO₂H(2)

(t) HOCH₂CH₂—COCO₂C₂H₅(3)

(u) (CH₃)₂N—(CH₂)₄—COCO₂H (v) 2-nitrophenyl-CH₂CH₂COCO₂C₂H₅(4)

(w) 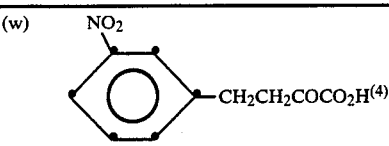 4-nitrophenyl-CH₂CH₂COCO₂H(4)

(x) 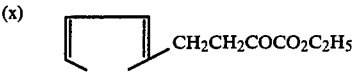 thienyl-CH₂CH₂COCO₂C₂H₅

(y) 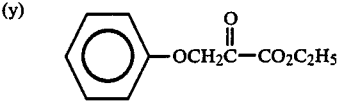 phenyl-OCH₂C(O)—CO₂C₂H₅

(z) 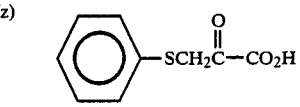 phenyl-SCH₂C(O)—CO₂H (aa) 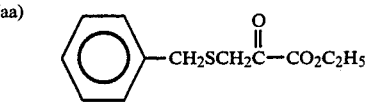 phenyl-CH₂SCH₂C(O)—CO₂C₂H₅

(1) Protected as the N—Cbz derivative.
(2) 2-Imidazole NH protected as the N—benzyl derivative.
(3) Protected as the O—benzyl derivative.
(4) Precursor to m-amino derivative by $H_2$/Pd.

TABLE II
Additional Products of Formula I:

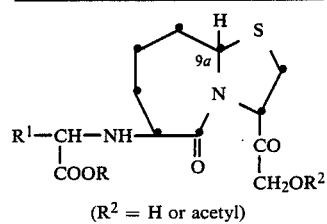

($R^2$ = H or acetyl)

| | R | $R^1$ | (9a) Stereochemistry |
|---|---|---|---|
| (1) | n-C₄H₉— | phenyl-CH₂CH₂— | S |
| (2) | CH₂=CH—CH₂— | phenyl-CH₂CH₂— | R |
| (3) | C₂H₅— | phenyl-CH₂CH₂— | S |
| (4) | C₂H₅— | phenyl-CH₂CH₂— | R |

TABLE II-continued
Additional Products of Formula I:
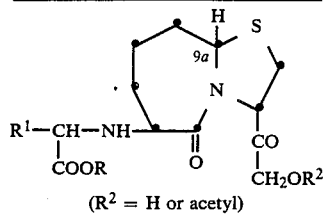
(R² = H or acetyl)
| R | R¹ | (9a) Stereochemistry |
|---|---|---|
| (5) C₆H₅—CH₂ | C₆H₅—CH₂CH₂ | S |
| (6) CH₃— | C₆H₅—CH₂CH₂ | S |
| (7) H— | C₆H₅—CH₂CH₂ | R |
| (8) CH₃— | C₆H₅—CH₂CH₂ | R |
| (9) CH₃— | C₆H₅—CH₂CH₂ | R |
| (10) CH₃— | C₆H₅—CH₂CH₂ | S |
| (11) H | C₆H₅—CH₂CH₂— | S |
| (12) C₂H₅— | C₆H₅—CH₂CH₂CH₂ | R |
| (13) H | Cl—C₆H₄—CH₂— | R |
| (14) H | (indol-3-yl)—CH₂ | R |
| (15) H | (2-Cl-C₆H₄)—CH₂CH₂ | R |

TABLE II-continued
Additional Products of Formula I:

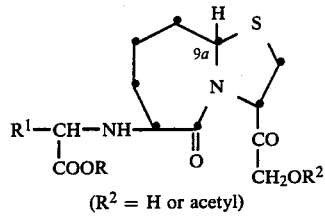

($R^2$ = H or acetyl)

| R | $R^1$ | (9a) Stereochemistry |
|---|---|---|
| (16) $C_2H_5$— | indol-3-yl-$CH_2CH_2$— | R |
| (17) $C_2H_5$— | 4-phenoxyphenyl-$CH_2CH_2$— | R |
| (18) $C_2H_5$— | $CH_3O$-C$_6$H$_4$-$CH_2CH_2$— | S |
| (19) $C_6H_5CH_2$— | HO-C$_6$H$_4$-$CH_2CH_2$— | R |
| (20) $CH_3$— | 2-naphthyl-$CH_2CH_2$— | S |
| (21) $C_2H_5$ | 1-naphthyl-$CH_2CH_2$— | R |
| (22) $C_2H_5$— | $CH_3S$—$CH_2CH_2$— | S |
| (23) $CH_3$ | $(CH_3)_2$—$CH$—$CH_2$— | S |
| (24) $C_2H_5$— | $CH_3CH_2CH_2CH_2$ | R |
| (25) $CH_3$— | F-C$_6$H$_4$-$CH_2CH_2$— | R |
| (26) H | $NH_2(CH_2)_5$— | S |
| (27) H | 3-($CH_2NH_2$)-C$_6$H$_4$-$CH_2CH_2$— | S |
| (28) H | imidazol-4-yl-$CH_2CH_2$— | S |
| (29) $C_2H_5$ | $HOCH_2CH_2$— | R |

TABLE II-continued

Additional Products of Formula I:

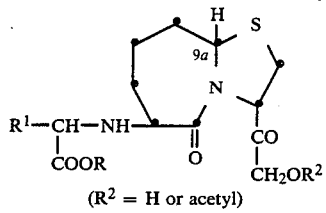

($R^2$ = H or acetyl)

| | R | $R^1$ | (9a) Stereochemistry |
|---|---|---|---|
| (30) | H | (CH₃)₂N—(CH₂)₄— | S |
| (31) | $C_2H_5$ | 2,4-dichlorophenyl-CH₂CH₂— | S |
| (32) | H | (2-aminophenyl)-CH₂CH₂— | R |
| (33) | $C_2H_5$ | (2-aminophenyl)-CH₂CH₂— | S |
| (34) | $C_2H_5$ | (thien-2-yl)-CH₂CH₂— | S |
| (35) | $C_2H_5$ | phenyl-O—CH₂ | S |
| (36) | H | phenyl-S—CH₂ | R |
| (37) | $C_2H_5$ | phenyl-CH₂SCH₂ | R |

What is claimed is:
1. A compound which is a member of the group:
    6(S)-[1(S)-(benzyloxycarbonyl-3-phenylpropyl-)amino]octahydro-5-oxo-9a(R)-thiazolo[3,2-a]azepine-3-(R)[2-diazo-1-oxoethane];
    6(S)-[1(S)-(ethoxycarbonyl-3-phenylpropyl-)amino]octahydro-5-oxo-9a(R)-thiazolo[3,2-a]azepine-3-(R)[2-diazo-1-oxoethane];
    6(S)-[1(S)-(benzyloxycarbonyl-3-phenylpropyl-)amino]octahydro-5-oxo-9a(R)-thiazolo[3,2-a]azepine-3-(R)[2-hydroxy-1-oxoethane];
    6(S)-[1(S)-(ethoxycarbonyl-3-phenylpropyl-)amino]octahydro-5-oxo-9a(R)-thiazolo[3,2-a]azepine-3-(R)[2-hydroxy-1-oxoethane]; and,
    6(S)-[1(S)-(carboxy-3-phenylpropyl)amino]octahydro-5-oxo-9a(R)-thiazolo[3,2-a]azepine-3-(R)[2-hydroxy-1-oxoethane].

* * * * *